US005945111A

United States Patent [19]

Esser

[11] Patent Number: 5,945,111

[45] Date of Patent: Aug. 31, 1999

[54] METHOD FOR APPLYING A COSMETIC AGENT BY ELECTROSTATIC SPRAYING

[75] Inventor: Isabelle C. Esser, Merseyside, United Kingdom

[73] Assignee: Unilever Patent Holdings B.V., Vlaardingen, Netherlands

[21] Appl. No.: 08/949,858

[22] Filed: Oct. 14, 1997

Related U.S. Application Data

[63] Continuation of application No. 08/436,234, filed as application No. PCT/GB93/02369, Nov. 18, 1993, abandoned.

[30] Foreign Application Priority Data

Nov. 18, 1992 [GB] United Kingdom .................. 9224191

[51] Int. Cl.$^6$ .............................. A61K 9/10; A61K 7/00

[52] U.S. Cl. ............................ 424/401; 424/45; 424/47; 424/78.02; 424/78.03; 424/70.1; 424/70.11; 424/59; 424/65; 514/937

[58] Field of Search ............................... 424/401, 45, 47, 424/78.02, 78.03, 70.1, 70.11, 59, 65; 514/937

[56] References Cited

U.S. PATENT DOCUMENTS 4,829,996 5/1989 Noakes et al. .

FOREIGN PATENT DOCUMENTS

| | | |
|---|---|---|
| 197242 | 10/1986 | European Pat. Off. . |
| 0 224 352 | 6/1987 | European Pat. Off. . |
| 0 501 725 | 9/1992 | European Pat. Off. . |
| 523961 | 1/1993 | European Pat. Off. . |
| 523962 | 1/1993 | European Pat. Off. . |
| 523963 | 1/1993 | European Pat. Off. . |
| 56-097214 | 8/1981 | Japan . |
| 2 128 900 | 5/1984 | United Kingdom . |
| 90/00446 | 1/1990 | WIPO . |

OTHER PUBLICATIONS

WPI Abstract Accession No. 81–68872D/38.

*Primary Examiner*—Raj Bawa

*Attorney, Agent, or Firm*—Pillsbury Madison & Sutro, LLP

[57] ABSTRACT

A method of delivering a cosmetic agent to the body, comprising electrostatically spraying thereon a cosmetic composition comprising said cosmetic agent, the composition having a resistivity of less than $10^4$ ohm cm. Apparatus for carrying out the method comprises a reservoir for the composition, delivery means, a voltage generator, and control means for applying the voltage from the generator to the delivery means to electrostatically spray the composition. The cosmetic agent may comprise an antiperspirant or other type of personal cosmetic product.

11 Claims, 1 Drawing Sheet

METHOD FOR APPLYING A COSMETIC AGENT BY ELECTROSTATIC SPRAYING

This application is a continuation of application Ser. No. 08/436,234, filed as PCT/GB93/02369 Nov. 18, 1993 now abandoned.

FIELD OF THE INVENTION

This invention relates to a system for delivering cosmetic agents to various parts of the body, and particularly to methods and apparatuses for delivering cosmetic agents to the skin or the hair using the principle of electrostatic spraying. The invention relates especially to electrostatically sprayable compositions of low resistivity via which cosmetic agents can be so delivered.

BACKGROUND OF THE INVENTION

Conventionally, cosmetic agents for application to various parts of the body are frequently delivered by means of spraying, particularly when the cosmetic agent is to be applied to a large or non-localised target area such as the skin or the hair. Such spraying regimes, frequently referred to simply as "aerosols", rely on a pressurized propellant-containing can or a manually operable pump-action spray device to generate a spray of the product to be delivered, which is generally a solution or mixture of the cosmetic active in one or more solvents or vehicles such as water and/or ethanol, frequently with one or more other adjunct materials as conventionally used in personal product formulations.

These known aerosol delivery systems are inefficient and represent uneconomical use of cosmetic raw materials. They are often also bulky, heavy and expensive, and are noisy to use. A further problem associated with these known aerosol delivery systems is that they have generally limited sensory appeal, especially in that they generate cold, wet sprays. Furthermore, with these sprays there is only partial capture of product at an intended site and thus significant waste through loss of cosmetic active material and additional ingredients (if present) to the atmosphere, which also results in unwanted atmospheric mists and contamination to the user's eyes or other body parts, which may present respiratory or other health problems to the user.

Conventional aerosol sprays frequently employ volatile organic compounds as propellants, which are now well recognised as being environmentally unfriendly, possibly hazardous to health and indeed are being legislated against in many countries of the world. Conventional sprays also suffer from the inability to provide 100% coverage of a given target, e.g. all areas of the surface of hair fibres, all areas of the surface of the skin (which is not flat and presents a very rough terrain on a microscopic scale), or areas of the body surface which are ordinarily, or as a result of some disability, difficult to reach.

In our copending published European patent application EP-A-0523964 the disclosure of which is incorporated herein by reference, there is disclosed a novel system for delivering a cosmetic agent to the body, comprising electrostatically spraying the cosmetic agent thereon. In the disclosed apparatuses and methods the cosmetic agent is provided in a reservoir in the form of an electrostatically sprayable composition. In communication with the reservoir is at least one delivery means to which is applied a high voltage from a suitable power source in order to electrically charge the composition therein so as to electrostatically spray it from a nozzle part of the delivery means. Cosmetic agents delivered to the skin or hair using these novel systems give advantageous practical results, particularly 360° wrap-around, high product capture, silent, invisible and non-wet sprays and more efficient use of cosmetic raw materials.

In accordance with this earlier proposal, the compositions containing one or more cosmetic agents to be delivered must be electrostatically sprayable. This means that, in addition to controlling system parameters such as flow rate, viscosity of the composition and applied voltage, the composition must have appropriate electrical characteristics, notably resistivity, which permit of electrostatic spraying. The disclosed resistivities fall within the range from about $10^4$ to about $10^{12}$ ohm cm, more preferably from about $10^6$ to about $10^{10}$ ohm cm. In order to satisfy this criterion, the preferred compositions are substantially non-aqueous or contain only a small amount of water, e.g. less than 10% by weight, since keeping the proportion of low resistivity components (i.e. mainly water) to a minimum allows the higher resistivity characteristics of more insulating solvents and other materials present to dictate the overall electrical characteristics of the cosmetic agent-containing composition.

In the light of the above wisdom in the art, one problem which arises is that whilst electrostatic spraying would seem to present solutions to the majority of the problems associated with prior art personal product spraying systems, there are significant limitations imposed on personal product formulations in terms of their composition, especially in the content of major ingredients such as solvents and carriers/vehicles for the cosmetic active(s). In particular, in order to achieve suitably high resistivities for satisfactory spraying in accordance with the prior art teaching, electrostatically sprayable compositions must still contain major proportions of non-aqueous ingredients, thereby to some extent negating advantages over conventional aerosols such as cost, atmospheric innocuousness and acceptability, and sensory appeal for the user.

In EP-A-0501725 (the disclosure of which is incorporated herein by reference) electrostatic spraying of what are defined as "low resistivity" liquids is disclosed, such as aqueous-, alcoholic- or aqueous/alcoholic-based liquids, for example as commonly used in a variety of personal care products. By "low resistivity" is meant resistivities of between 10 and $10^4$ ohm cm, to which the disclosure and teaching of the application is limited. The invention disclosed in the reference lies in the finding that liquids of such relatively low resistivities can in fact be sprayed by electrostatic means to give a fine mist spray (e.g. with droplet size no greater than 150 $\mu$m), contrary to conventional wisdom in the art. Normally, with practical flow rates as demanded by personal products, it had not previously been possible to produce satisfactory and sufficiently fine sprays (for what was considered to be an appropriate level of sensory acceptability) with liquids of resistivities lower than about $10^7$ ohm cm. According to the disclosed earlier invention, however, this problem is solved by the use of a special construction and design of spray nozzle including an orifice from which the composition emerges in the form initially of a ligament which subsequently breaks up into a fine mist of droplets.

Another reference which mentions electrostatic spraying of aqueous liquids is EP-A-0152446, which relates to a special construction of spray head which enables certain aqueous liquids to be satisfactorily sprayed under ligamentary mode electrostatic spraying, as had previously only been attainable with oil-based formulations. Whilst the disclosed liquids suitable for spraying include distilled water and alcohol, resistivities only as low as $10^4$ ohm cm are mentioned (with the exception of a spurious lower limit on resistivity of 50 ohm cm, though this is only in the context of agricultural chemicals or coating compositions).

In the light of the teaching of EP-A-0501725, which is based on prior art represented specifically by EP-A-0152446, it is clear that neither of these references envisage practical electrostatic spraying of personal care liquids having resistivities of less than $10^4$ ohm cm. Furthermore, in EP-A-0152446 the construction of the disclosed spray head renders it unsuitable for small scale personal use for reasons of safety from high voltage electrostatic shocks and physical danger from and aesthetics of the sharp edged or pointed components of the device.

During our extensive investigations into the possibilities for electrostatically spraying low resistivity liquids, especially very low resistivity cosmetic agent-containing compositions, we have surprisingly found that quite acceptable sensory results can be obtained with sprays of a significantly coarser droplet size (for example even of the order of up to about 300 $\mu$m or more) than has hitherto been recognised in the art, particularly in EP-A-0501725. The importance of this observation is that in order to electrostatically spray personal product formulations at practical flow rates in a manner which gives aesthetically satisfactory results, one is not necessarily constrained by compositions having a minimum resistivity, even with conventional nozzle designs, as is suggested to be the case in EP-A-0501725. In the light of this new realisation, we have gone on to find, most surprisingly, that it is indeed possible to electrostatically spray, with aesthetically satisfactory results, cosmetic agent-containing compositions which have extremely low resistivities, i.e. less than about $10^4$ ohm cm.

In the context of such extremely low resistivity liquids, one problem which is known from the art to be potentially deleterious to successful spraying is the relatively high conductivity of the liquid, which can lead to problems (both practically and as regards safety for the user) of corona discharge. We have also found this to be especially important in terms of the carriage of electrical charge on the spray droplets from the spray nozzle to the target surface on the body. As conductivity of the liquid increases, so does the amount and/or rate of charge transfer, i.e. electric current, between the spraying device and the target, such that there is potentially a risk of overcharging of the target and thus electrical shocks to the user, which are of course unwanted. We have further found during our investigations that despite what would appear to be a serious practical problem with spraying extremely low resistivity liquids, one can in fact define optimum combinations of system parameters, including applied voltage and electrical characteristics of the composition to be sprayed, which fall within a "safe window" within which the current between spraying apparatus and target surface can be controlled within safe limits and thus the potential for electrical shocks minimised.

On the basis of the above findings, therefore, we have found that it is possible to successfully and safely deliver cosmetic agents to the body by electrostatic spraying from relatively conductive cosmetic compositions having resistivities of arround $10^4$ ohm cm and less. Such compositions may frequently be substantially aqueous, alcoholic or aqueous/alcoholic for example, which makes for simpler and cheaper technology whilst retaining the aforementioned sensory and environmental benefits of electrostatic spraying of personal products and also opens up greater freedom in the choice and combinations of cosmetic actives and auxiliary ingredients in personal product spraying technology.

SUMMARY OF THE INVENTION

Accordingly, in a first aspect the present invention provides a method of delivering a cosmetic agent to the body, comprising electrostatically spraying thereon a cosmetic composition comprising said cosmetic agent, the composition having a resistivity of less than about $10^4$ ohm cm.

In more detail, the method of this aspect of the invention preferably comprises:

(a) providing an apparatus which includes:
  (i) a reservoir containing an electrostatically sprayable cosmetic composition comprising said cosmetic agent and having a resistivity of less than about $10^4$ ohm cm;
  (ii) at least one delivery means in communication with the reservoir;
  (iii) a high voltage generator powered from an electricity source;
  (iv) control means for selectively applying the high voltage from the generator to the or each delivery means; and (b) actuating the said control means to electrostatically spray the cosmetic composition from the or each delivery means onto the body at an intended site.

In a second aspect, the present invention provides an apparatus for delivering a cosmetic agent to the body, comprising:

(a) a reservoir containing an electrostatically sprayable cosmetic composition comprising said cosmetic agent and having a resistivity of less than about $10^4$ ohm cm;

(b) at least one delivery means in communication with the reservoir;

(c) a high voltage generator powered from an electricity source;

(d) control means for selectively applying the high voltage from the generator to the or each delivery means to electrostatically spray the cosmetic composition from the or each delivery means.

In practical embodiments of the above aspects of the invention, it is particularly preferred that the combination of at least the electrical characteristics of the composition being sprayed, the magnitude of the applied high voltage and the flow rate of the composition from the delivery means (either the single delivery means or the plurality of delivery means together) is such that the electric current between the delivery means and the target site on the body is insufficient to cause electrical shock between the body and earth.

DETAILED DESCRIPTION OF THE INVENTION AND PREFERRED EMBODIMENTS

Figure 1:
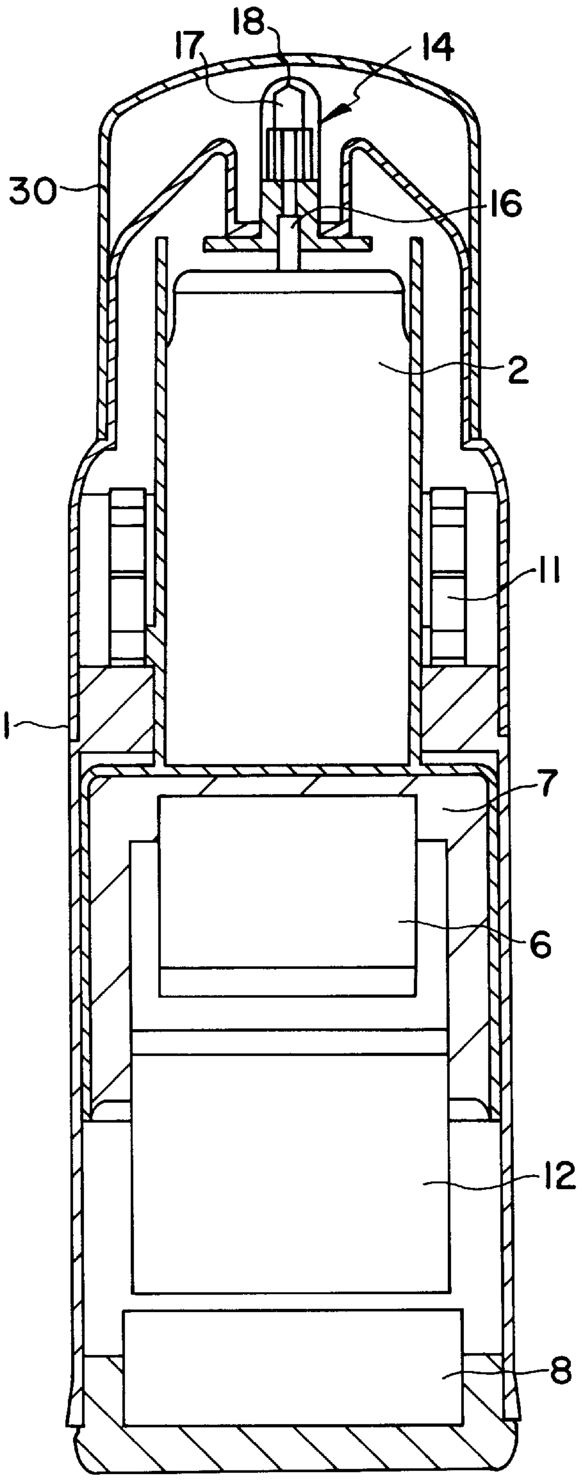

The various aspects of the present invention, and in particular exemplary embodiments thereof, will now be described in detail.

As used herein, the term "body" is intended to include both the hair and the skin. While in the context of skin the invention is useful in delivering cosmetic agents which provide one or more cosmetic or sensory benefits such as cleaning, conditioning or the like or those which are normally perceived by vision, smell, touch or feeling, the invention is also useful in delivering cosmetic agents to the hair and/or scalp, for example for the purpose of cleaning, conditioning, styling or other cosmetic or even pharmaceutical (e.g. antidandruff) treatment.

Because the present invention makes it possible to electrostatically spray cosmetic compositions without the need to so carefully control resistivity within defined limits as in the prior art, the formulation and collective electrical properties of the various components of the cosmetic compositions are less critical and provide greater freedom in formulating personal products in terms of conventional criteria such as cosmetic and sensory benefits, product stability, efficacy and the like, rather than having the emphasis placed solely on the overall electrical properties of the composition as has hitherto had to be considered paramount. Thus, in the cosmetic compositions according to the present invention, a very wide range of cosmetic actives, solvents, carriers etc, and various adjunct materials may be used with considerably greater flexibility than has hitherto been the case in the art of spraying personal product liquids by electrostatic means.

Because the present invention is limited to cosmetic compositions having resistivities of less than about $10^4$ ohm cm, and since this is characteristically lower than the resistivity of distilled water (at 25° C.), in preferred embodiments of the invention the cosmetic composition to be sprayed contains one or more charged species, for example ionic species, which reduce the resistivity of the (preferably) liquid composition to below $10^4$ ohm cm. The resistivity of the composition may for example be as low as $10^1$ ohm cm, or even lower, though the most suitable resistivity for a given composition to be sprayed in a given system will usually depend on other system parameters such as voltage and flow rate.

The charged species present in the compositions of the invention may be a cosmetic active itself which it is desired to deliver to the body, or alternatively may be an adjunct material which is included in order to give the composition the desired conductivity and/or other electrical characteristics, as described further below.

Frequently, in the commercial production of cosmetic ingredients small amounts of impurities such as salts and metals may be present which may themselves modify the resistivity of the pure material to some extent. Any additions of adjunct materials for the purpose of changing the resistivity of cosmetic compositions of the invention therefore preferably take this into account.

As examples of cosmetic actives which may be included in the compositions of the invention and which may be expected to carry sufficient charge to give the compositions the required resistivity without necessarily the presence of other charged species to modify the resistivity, are the following:

1. antiperspirant actives—e.g aluminium salts
2. antimicrobial/antibacterial agents—e.g. zinc salts
3. ionic antidandruff agents—e.g. zinc pyridinethione
4. ionic polymers—e.g. hair resins
5. other charged species useful in personal products for example for hygiene or deodorant purposes.

Further examples of suitable charged actives which may be included in compositions of the invention, and which may or may not require the presence of auxiliary ingredients for the purpose of adjusting the resistivity of the composition to the required level, are skin or hair benefit substances which are characteristically charged (either positively or negatively, or in the form of zwitterions) in the environment of the composition into which they are incorporated. Quaternary ammonium compounds e.g. quaternary silicones, hydrolysed proteins and certain natural substances such as gums, starches and derivatives thereof are examples of such materials.

The following is a list of further exemplary cosmetic actives which may be employed in cosmetic compositions for delivery by electrostatic spraying in accordance with the invention. Many of these listed actives may be expected to require the presence of one or more auxiliary ingredients for the purpose of adjusting the resistivity of the composition to the required level. However, for any given active, since the environment within the composition into which it is incorporated, in particular with respect to other ingredients and any solvents or carriers which are present, may often affect the degree to which it is electrically charged when the composition is provided for spraying, it will be a simple matter of observation and/or experiment for the skilled person to combine with the active, if necessary, a suitable amount of one or more resistivity adjusting substances which give the composition the required resistivity in accordance with the invention.

1. potent actives (i.e. those conventionally used in very small quantities—e.g. perfumes, essential oils;
2. skin and hair moisturisers, e.g. 2-hydroxyalkanoic acids, and acid-soap complexes thereof, polyols such as glycerol and glycols, 2-pyrrolidone-5-carboxylic acid, and other emollients or humectants;
3. occlusive materials, e.g. occlusive oils;
4. sun-protective materials, e.g. sunscreens, particularly UV-absorbing sunscreens;
5. after-sun care materials, e.g. materials for treating sunburn;
6. skin conditioning agents, e.g. agents which smooth or soften the skin;
7. skin colouring agents, e.g. artificial tanning products such as compositions containing dihydroxyacetone (DHA);
8. antibacterial or antifungal materials;
9. insect repellents;
10. astringent materials, e.g. hydrolisable tannins, phenolic acids associated with tannins, phenols associated with tannins, flavonoid compounds, natural extracts providing astringency, organic astringents and inorganic astringents (particularly salts of aluminium, zinc, iron (III), copper or silver);
11. skin cleansers and make-up or other cosmetic removers;
12. massage oils;
13. skin nutrients and healing agents, including lipsalves;
14. spot and skin blemish treatment materials, including wart removers;
15. skin whiteners and agents for treating pigmentation disorders, e.g. freckles;
16. antiseptics and disinfectants;
17. anti-ageing agents, e.g. for treating wrinkles or preventing development thereof;
18. agents for treating sensitive skin.
19. surfactants, e.g. selected from anionic, cationic, amphoteric, zwitterionic and nonionic surfactants and mixtures thereof;
20. hair conditioning agents, i.e. materials which impart one or more visual or tactile benefits such as softness, smoothness, shine, non-flyaway, ease of dry and/or wet combing, e.g. cationic surfactants, cationic polymers, volatile and/or non-volatile silicones or derivatives thereof, quaternary ammonium salts having at least one long chain alkyl or alkenyl group, protein hydrolysates, quaternized protein hydrolysates, perfluoropolyether materials, fatty alcohols, and mixtures thereof;
21. hair styling agents, i.e. materials which give enhanced body and feel to hair to enable it to hold a style, e.g. various polymers, gums and resins, for example adhesive and/or resinous hydrocarbon materials such as per-alk(en)yl hydrocarbon materials, silicone/siloxane gums or resins, waxes, chitosan and derivatives, salts and complexes thereof, and mixtures thereof;

22. hair straightening agents;
23. colourants and dyeing agents;
24. antidandruff agents, e.g. zinc pyridinethione, Octopirox, Climbazole, Glycamil;
25. hair growth promoters or regulators, e.g. diacylglycerols, glucarolactams, glucarolactones, Minoxidol;
26. pearlescent and/or opacifying materials;
27. oils, e.g. silicone oils, oleic acid, hydrocarbons, isopropyl myristate, oleyl alcohol, oleates, squalene, sunflower seed oil, rapeseed oil, other plant-derived oils, mineral oil;
28. proteins, vitamins, nutrients, stimulants, antiradicals, astringents;
29. herb or other plant extracts, essential oils, etc;
30. other adjunct materials commonly used in cosmetic compositions, e.g. buffering and/or pH adjusting agents, perfumes, colourings, preservatives, proteins, etc.
31. cosmetic foundation materials, e.g. creams or other compositions;
32. cosmetic mask formulas;
33. skin colour cosmetics e.g. blushers;
34. eye cosmetics such as eyeshadows;
35. fun make-up materials;
36. lip colouring materials and varnishes;
37. coloured polymers and waxes;
38. eye cosmetics such as eyeliners, mascaras and the like;
39. nail colours, polishes, varnishes, hardeners, protectors, etc.

Auxiliary ingredients which may be employed as necessary in combination with the cosmetic active or actives in compositions of the invention to reduce the resistivity thereof to the required level include charged, preferably ionic, species such as salts. Examples of suitable salts include sodium chloride, potassium chloride, ammonium chloride, sulphates of these cations, and other salts frequently employed in known cosmetic compositions. Suitable amounts of such resistivity adjusting ingredients will generally be dictated by the degree to which the resistivity is to be adjusted and will be readily determined by simple observation or experiment by the skilled person.

The cosmetic compositions to be electrostatically sprayed in accordance with the invention preferably comprise a major proportion of one or more solvents or vehicles/carriers for the cosmetic agent(s) to be delivered. Preferably, and especially when the active is charged/ionic, the composition will be in the form of a solution of the active in the one or more solvents. The compositions of the invention preferably comprise at least 80% by weight solvent, more preferably at least 90%, and even more preferably greater than 95% by weight solvent.

The preferred solvent is water e.g. distilled or even deionised water (though the latter is inherently less conductive than the former). Other suitable solvents, which may be used alone or in mixtures with each other or in combination with water, include alcohols, especially lower alcohols such as ethanol, but also polyols and certain esters, for example: isopropyl alcohol, propylene glycol, dipropylene glycol, phenylethyl alcohol, glycerol, 1,3-butane diol, 1,2-propane diol, isoprene glycol, diethyl phthalate.

Broadly speaking, therefore, preferred relatively conductive cosmetic compositions suitable for delivery by means of electrostatic spraying in accordance with the present invention include any of the following:

inorganic or organic salt(s) in water
inorganic or organic salt(s) in water/ethanol mixtures
antiperspirant solutions
polymer(s) in ethanol and/or water
antidandruff or hair growth compositions
enzyme solutions
bactericide solutions
mixtures of any of the above systems.

Specific examples of relatively conductive cosmetic compositions of these classes which have been found to be electrostatically sprayable with satisfactory sensory results are given in the Examples further below.

Whilst resistivity is important in ensuring electrostatic sprayability of a composition, and does indeed define a limit on those compositions which are within the scope of the present invention, a further property which may in certain cases be desirable to select or adjust is ionic strength. This will apply particularly in the case of cosmetic compositions containing one or more ionic species, either as the cosmetic active or as a resistivity adjusting material, or as both. For an electrolyte solution the ionic strength I is given by the formula:

$$I = \tfrac{1}{2}\sum_i m_i z_i^2.$$

where z is the valency on the ionic species i and m is the molal concentration thereof, the summation being continued over all the different ionic species i in the solution.

Because ionic strength depends upon the valence and concentration of ionic species in the composition, whereas resistivity reflects principally the mobility of charged species, ionic strength will, in the case of ionic species, be one parameter which may be important in determining (for a given flow rate for example) the amount or rate of charge transfer between the delivery means of the electrostatic spraying apparatus and the intended spray target on the body. As mentioned previously, a particularly preferred property of the spraying systems of the present invention is that the flow of current between the apparatus and the spray target on the body, and thus the propensity for the occurrence of electrical shocks, is limitatively controlled. Accordingly, for this purpose selection and/or adjustment of ionic strength of a composition to be sprayed, as well as other parameters of the spraying system (as herein described), may be necessary in order to achieve consumer acceptability and safety of the spraying system.

It is difficult to place rigid numerical limitations on the ionic strength of a composition for use in accordance with the present invention, owing to the variability of other parameters of the system which too affect rate of charge transfer between the apparatus and the target, as well as the wide variety of ingredients, both charged species and uncharged species, which may be included in the composition. Generally speaking, however, suitable ionic strengths are readily determinable by experience and/or trial and error in the context of a given spraying system, and this will be readily appreciated by persons skilled in the art.

Compositions of a wide range of viscosities may be suitable for use in the present invention, but suitably the viscosity is in the range of from about 0.1 to about 5000 mPas, more preferably from about 0.1 to about 1000 mPas, even more preferably from about 0.5 to about 500 mPas (at 25° C.). If desired or as necessary one or more viscosity adjusting agents may be included. Examples of such agents are well known in the art and include salts, e.g. alkali metal or ammonium halides, polymers, e.g. heteropolysaccharide gums, conventional thickening materials such as clays, thickening silicas and certain cellulose derivatives, and oils and polar oil thickeners such as cosmetic oils, waxes, glycerides and suitable amphiphiles with melting points of for example >20° C.

In preferred embodiments of the apparatus and method of the invention, preferred voltages generated by the high voltage generator from the power source are in the range of from about 3 to about 20 kilovolts, more preferably from about 4 to about 12 kilovolts. In the context of the present invention, where relatively conductive compositions are being sprayed, i.e. with resistivities of less than about $10^4$ ohm cm, we have found that it is surprising that such preferred relatively low voltages can be used successfully, given that the general wisdom in the art has hitherto been that the lower the resistivity of the composition, the higher is the voltage necessary to achieve satisfactory spraying with sufficiently fine droplet size.

As previously mentioned, we have found that quite adequate, and in many cases sensorily satisfactory, sensory results can be obtained with coarser droplet size sprays than has hitherto been appreciated, so the ability to spray relatively conducting liquids at relatively low voltages is particularly advantageous as regards size and cost of the apparatus and safety aspects thereof. The present invention is not limited however to the spraying of compositions with relatively coarse droplet sizes, but it includes sprays of any droplet size (even relatively fine sprays, e.g. with droplet sizes of down to about 20 to 40 or less) appropriate to the product in question and the other parameters, both constructional and operational, of the spraying system. In preferred embodiments of the invention, however, the average particle size of the electrostatic sprays is large enough so as to prevent or minimise the generation of respirable fractions, which is often important in cosmetic systems where inhalation of potentially harmful or unwanted components of such compositions is to be avoided. Preferably, the droplets of the sprays produced in the invention have an average particle size of at least about 50 $\mu$m, more preferably at least about 60 or 70 $\mu$m. In many practical embodiments of the invention average particle sizes of up to about 400 $\mu$m may be tolerated, though sizes up to about 300 or 350 $\mu$m will generally be more preferred. Too high a droplet size tends to give rise to a significantly "wet" sensory feeling from the spray, which may set an upper practical limit on spray droplet sizes for some cosmetic applications. Most preferred in the invention however are sprays having average droplet sizes in the range of from about 50 up to about 150 or 200 $\mu$m.

The average droplet size of sprays according to the invention may be selected or controlled by known techniques in the art, principally by appropriate selection of the system operating parameters, especially an appropriate combination of flow rate of the composition through the delivery means and the applied voltage. The size of a nozzle providing the output from the delivery means may also be selected appropriate to other parameters for the purpose of optimizing desired average spray droplet sizes. In this respect the disclosure of EP-A-0523964, mentioned hereinabove, is relevant to the systems of this invention, the disclosure in which is incorporated herein by reference.

Applied voltage is in fact another parameter of the spraying systems in accordance with the invention which, like ionic strength, may be selected or adjusted in order to control the amount or rate of charge transfer between the spraying apparatus and the body target. Higher applied voltages generally lead to greater amounts of material delivered to the target, and so for a given composition and spraying apparatus, applied voltage may be usefully controlled or adjusted in order to obtain a necessary or desired amount or rate of charge transfer to the target, thereby avoiding unwanted and possibly harmful charge build up leading to electrical shocks. As with ionic strength, a suitable voltage within the above mentioned guideline limits will depend upon other parameters and characteristics of the spraying system, and may be optimised through experience or trial and error by the skilled person.

For use in the present invention, the hardware and electrical componentry and circuitry may be of any suitable construction and design. The art of electrostatic spraying contains many examples of suitable apparatus which may be used in the present invention and such disclosures of such apparatus or particular features thereof may be applied either singly or in combination to the spray systems of the present invention.

Examples of suitable electrostatic spraying hardware include those disclosed in EP-A-0523964 mentioned hereinabove. An example is shown in FIG. 1 of the accompanying drawings.

In the embodiment of the apparatus aspect of the invention as shown schematically in FIG. 1, the spraying apparatus is constructed with a similar size, shape and weight to a conventional aerosol spray, so as to form a hand-held unit which is easy to manipulate and use and suitable for personal use. The apparatus comprises an elongate housing 1, which is preferably electrically insulating, e.g. of a plastics material, within which the electrical and other hardware components of the apparatus are mounted.

Towards the base of the apparatus is housed a battery 8, such as a conventional low voltage, e.g. 1.5 to 12, particularly 9, volts, cell, which location allows ready access to the battery for the purpose of replacement when necessary. Indicated by numeral 6 is the high voltage generator, which converts the low voltage from the battery 8 into the high voltage of for example between about 12 and 18 kilovolts, which is required for raising the cosmetic composition to be sprayed to the high electric potential necessary to effect electrostatic spraying thereof. Suitable components of the high voltage generator 6 are well known in the art and comprise principally a coil or transformer to perform the voltage step-up function. If desired or as necessary, various packing elements of electrically insulating material, such as that shown as 7 in FIG. 1, may be provided in order to increase the safety aspect of the high voltage apparatus and to reduce unwanted leakage paths to earth when the apparatus is in use.

Connected between the battery 8 and high voltage generator 6, as well as between the high voltage generator 6 and the remaining electrical components of the apparatus, are one or more circuit boards 12 containing any necessary auxiliary electrical componentry for ensuring effective and satisfactory functioning of the apparatus. Such additional circuit board(s) 12 may comprise for example DC/AC (or vice versa) converters, as well as voltage adjustment means to control the high voltage applied to the product delivery means from which the composition to be sprayed is to be delivered.

In the upper region of the apparatus is mounted reservoir 2 which in this preferred embodiment is a bag-in-can type reservoir, as known per se in the art of personal products and spraying apparatus. The bag-in-can reservoir 2 constitutes a low pressure product feed mechanism whereby the composition to be sprayed is fed to the nozzle 14 of the apparatus ready for medium to high flow rate spray delivery.

In fluid communication, via a conduit 16, with the reservoir 2 is a nozzle 14, which is connected electrically to the high voltage electrics of the apparatus so that the composition within the nozzle is raised to the high electric potential necessary to effect its egress from the nozzle under electrostatic forces and thus the electrostatic spraying thereof. The nozzle 14 comprises an internal chamber 17 which terminates at the tip of the nozzle in an orifice 18 from which the product within the chamber 17 emerges under the influence of the electrostatic forces. If desired or as necessary, the apparatus may include feed means such as a pump (not shown in the Figure) to transfer composition from the reservoir 2 to the nozzle 14 at the required rate. Typically a positive pressure of from about 1 to 4 psi will be suitable for this purpose.

The configuration of the nozzle 14 in the region of the orifice 18 may vary and may be selected in association with other spraying parameters in order to give an optimised system both as regards spray properties and safety.

The apparatus is preferably provided with some kind of cap 30 for protecting the nozzle 14 and other delicate components in the upper region of the apparatus from physical damage or contamination when the apparatus is not in use.

Shown schematically in FIG. 1 as 11 is a manual trigger which constitutes control means for selectively energising the unit to apply the high voltage to the nozzle to electrostatically spray the product therefrom. The trigger 11, like the other elements of the apparatus subject to unwanted voltage leakage or shock risk, is preferably constructed and situated to minimise such problems, expedients for which are known in the art.

Further features of the apparatus of the present invention which may be elected and/or adjusted in order to optimise the spraying characteristics of the systems of the invention, in addition to those already mentioned, include for example: electric field strength in or in the region of the product delivery means, flow rate of the product to be sprayed from the reservoir to and out of the delivery means, size and configuration of the delivery means itself and construction and properties of any product feed mechanism utilised between the reservoir and the output of the delivery means. These aspects are described further in our earlier application just referred to, so will not be described further here.

The present invention is further illustrated by the following examples.

EXAMPLES

Listed below are examples of compositions which are relatively conductive and may be delivered to the body (i.e. the skin and/or the hair) by electrostatic means in accordance with the present invention. Suitable apparatus is that described in EP-A-0523964 mentioned above.

In each example the relevant electrical characteristics (which are measurable) of the composition are given, and in order to optimise the spraying system within the parameters described herein, especially with regard to limiting current flow between the apparatus and the body target so as to minimise the risk of electrical shocks, the applied voltage generated by the power source in the apparatus, as well as product flow rate, may be adjusted as necessary or as desired, though generally within the preferred limits described herein.

Example 1

Salts in distilled water

| salt | solution molarity (M) | ionic strength (M) | resistivity ( cm) |
|---|---|---|---|
| $Na_2SO_4$ | 0.2 | 0.6 | $3.6 \times 10^1$ |
| | 0.02 | 0.06 | $2.8 \times 10^2$ |
| | 0.002 | 0.006 | $2.07 \times 10^3$ |
| $MgSO_4$ | 0.2 | 0.8 | $7.4 \times 10^1$ |
| | 0.02 | 0.08 | $3.3 \times 10^2$ |
| | 0.002 | 0.008 | $4.2 \times 10^3$ |
| $Al_2(SO_4)_3$ | 0.2 | 3 | $5.3 \times 10^1$ |
| | 0.02 | 0.3 | $2.2 \times 10^2$ |
| | 0.002 | 0.03 | $1.5 \times 10^3$ |
| | 0.0002 | 0.003 | $8.3 \times 10^3$ |
| NaCl | 1 | 1 | $2.7 \times 10^1$ |
| $K_4P_2O_7$ | 0.3 | 3 | $2.4 \times 10^1$ |

Example 2

Ethanol-water mixture + salt (1) 0.283 g $Na_2SO_4$ in 20% water:80% ethanol
R = $5.6 \times 10^3$ cm
Ionic strength = 0.06M

Example 3

Ethanol-based anti-perspirants

| | % w/w |
|---|---|
| (1) Ingredient | |
| Rehydrol II AP active (ex Reheis) | 20 |
| Isopropyl myristate | 9 |
| DC 344 (silicone emulsion ex Dow Corning) | 17 |
| Distilled water | 3 |
| Ethanol | 51 |
| R = $2.99 \times 10^3$ cm | |
| (2) Commercially available SURE (trademark) antiperspirant containing mainly aluminium chlorohydrate as active | |
| R = $2.4 \times 10^2$ cm | |

Example 4

Resins (1) Carboxylated vinylacetate terpolymer neutralised at 90% by 2-amino-2-methyl-1-propanol
27.5% w/w in ethanol R = $5.27 \times 10^3$ cm
20% w/w in ethanol R = $4.5 \times 10^3$ cm
14% w/w in ethanol R = $4.9 \times 10^3$ cm
5% w/w in ethanol R = $3.1 \times 10^3$ cm
(2) Amphoteric acrylic resin used as fixative for hairspray
14% w/w in ethanol R = $1.8 \times 10^4$ cm

Example 5

Antidandruff solution

Commercially available ALL CLEAR (trademark) antidandruff shampoo, frequent use—containing Octopirox as active R=$4.53\times10^1$ cm Example 6

| Hair growth actives | |
|---|---|
| Ingredient | % w/w |
| (1) | |
| glucarolactone | 8 |
| water | 92 |
| R = 2.4 × $10^2$ cm | |
| (2) | |
| glucarolactone | 8 |
| ethanediol | 10 |
| ethanol | 10 |
| sodium hydroxide | 8 |
| water | 64 |
| R = 1.15 × $10^2$ cm | |

Example 7

| Enzyme solution | |
|---|---|
| Ingredient | % w/w |
| Lipolase 100L (ex Novo Nordisk A/S) | 0.1 |
| C9–11/EO5 alcohol ethoxylate (ex Kolb) | 7 |
| water | 96.9 |
| R = 3.6 × $10^3$ cm | |

Example 8

| Bactericide solution | |
|---|---|
| Ingredient | % w/w |
| Nisin (ex sigma) | 1 |
| sodium chloride | 3 |
| water | 96 |
| R = 2.63 × $10^1$ cm | |
| Ionic strength = 0.05M | |

COMPARATIVE EXAMPLE

A series of electrostatic spraying experiments were conducted to assess a variety of different spray attributes characteristic of various cosmetic sensory perceptions for each of two compositions, the first being a "control" composition having a relatively high resistivity and comprising pure ethanol, and the second being a "test" composition according to the invention having a relatively low resistivity and comprising an aqueous sodium chloride solution.

Each composition was assessed by a panel of trained experts, by spraying equal amounts onto the skin of the inner forearm, for each of the eleven attributes, as shown in the table of results below. The electrostatic spraying hardware and operating system parameters were identical for both compositions and all runs and were the same as used in the preceding Examples.

The results are shown in the table below. The figures quoted are the mean ratings, based on a numerical scale of 1 to 10 (10=highest) for each attribute.

RESULTS

| Attribute | Control Composition (Ethanol, resistivity = 2 × $10^6$ Ωcm, average measured spray droplet size = 80 μm) | Test Composition (Aqueous NaCl solution, resistivity = 5 × $10^3$ Ωcm, average measured spray droplet size = 155 μm) |
|---|---|---|
| Force of Spray | 1.3 | 1.1 |
| Mistiness | 2.7 | 2.3 |
| Spray width | 5.9 | 5.8 |
| Coldness | 5.0 | 4.8 |
| Tingly feel | 2.2* | 3.3 |
| Wetness during Application | 3.6 | 4.1 |
| Coolness | 6.6* | 5.3* |
| Wet appearance | 1.1 | 1.2 |
| Freshness | 5.3 | 4.8 |
| Wetness after Application | 0.7* | 1.7* |
| Wet feel (tactile) | 2.6 | 2.4 |

*significantly different at p = 0.05

The above results show that the composition of the invention gave at least as good, and for some attributes better, sensory results compared with ethanol, representative of the prior art.

I claim:

1. A method of delivering a cosmetic agent to skin or hair, comprising electrostatically spraying on the skin or hair, droplets of a cosmetic composition comprising said cosmetic agent using a voltage in the range of about 3 to about 20 kilovolts, the composition having a resistivity of less than $10^4$ ohm cm and the average size of the droplets of the electrostatic spray being in the range of 50 to 400 μm.

2. A method according to claim 1, comprising:

(a) providing an apparatus which includes:
  (i) a reservoir containing said electrostatically sprayable cosmetic composition comprising said cosmetic agent and having a resistivity of less than $10^4$ ohm cm;
  (ii) at least one delivery means in communication with the reservoir;
  (iii) a high voltage generator powered from an electricity source;
(iv) trigger means for selectively applying the high voltage from the generator to the delivery means; and
(b) actuating the said trigger means to electrostatically spray the cosmetic composition from the delivery means onto the body at an intended site.

3. A method according to claim 1 or claim 2, wherein the cosmetic composition comprises one or more charged compounds which reduce the resistivity of the composition to below $10^4$ ohm cm.

4. A method according to claim 3, wherein the charged compound is the said cosmetic agent.

5. A method according to claim 4, wherein the charged cosmetic agent is selected from the group consisting of antiperspirant actives; antimicrobial/antibacterial agents; ionic antidandruff agents; and mixtures of any of the foregoing agents.

6. A method according to claim 3, wherein the charged compound is other than the said cosmetic agent.

7. A method according to any one of claims 3 to 6, wherein the composition comprises the said charged compound in an amount sufficient to give the composition the said resistivity of less than $10^4$ ohm cm.

8. A method according to any one of claims 3 to 7, wherein the charged compound is a salt.

9. A method according to any preceding claim, wherein the cosmetic composition comprises at least 80% by weight of one or more solvents.

10. A method according to claim 1, wherein the cosmetic composition comprises a system selected from the group consisting of inorganic or organic salt(s) in water/ethanol mixtures; antiperspirant solutions; antidandruff or hair growth compositions; enzyme solutions; bactericide solutions; and mixtures of any of the foregoing systems.

11. A method according to claim 1, wherein the average droplet size is in the range 50 to 200 $\mu$m.

* * * * *